United States Patent [19]
Wallis

[11] Patent Number: 4,552,347
[45] Date of Patent: Nov. 12, 1985

[54] X-RAY APPARATUS COMPRISING A TABLE-TOP WHICH IS DISPLACEABLE IN THE LONGITUDINAL DIRECTION

[75] Inventor: Manfred Wallis, Hamburg, Fed. Rep. of Germany

[73] Assignee: U.S. Philips Corporation, New York, N.Y.

[21] Appl. No.: 555,845

[22] Filed: Nov. 28, 1983

[30] Foreign Application Priority Data

Dec. 2, 1982 [DE] Fed. Rep. of Germany ....... 3244579

[51] Int. Cl.⁴ .............................................. A61G 13/00
[52] U.S. Cl. .................................... 269/322; 378/209
[58] Field of Search ......................... 269/322, 323, 61; 108/137, 143; 378/209; 74/89, 21

[56] References Cited

U.S. PATENT DOCUMENTS 2,692,173 10/1954 Lowitzsch ........................ 378/209
3,399,578 9/1968 Lindabury et al. ............... 74/89.21
3,473,024 10/1969 Feiertag .............................. 378/209
4,164,656 8/1979 Krasznai et al. .

FOREIGN PATENT DOCUMENTS 8115418 10/1981 Fed. Rep. of Germany .

Primary Examiner—Robert C. Watson
Attorney, Agent, or Firm—Marc D. Schechter

[57] ABSTRACT

The invention relates to a patient table for an X-ray apparatus. The table has a table top which is displaceable in the longitudinal direction thereof. The table top is coupled to an endless chain which is guided by sprockets. One sprocket is driven by a motor. The coupling between the table top and the chain is realized by means of comb-like coupling elements which engage the chain. The coupling elements are arranged so as to be offset with respect to one another in the longitudinal direction of the table top.

5 Claims, 2 Drawing Figures

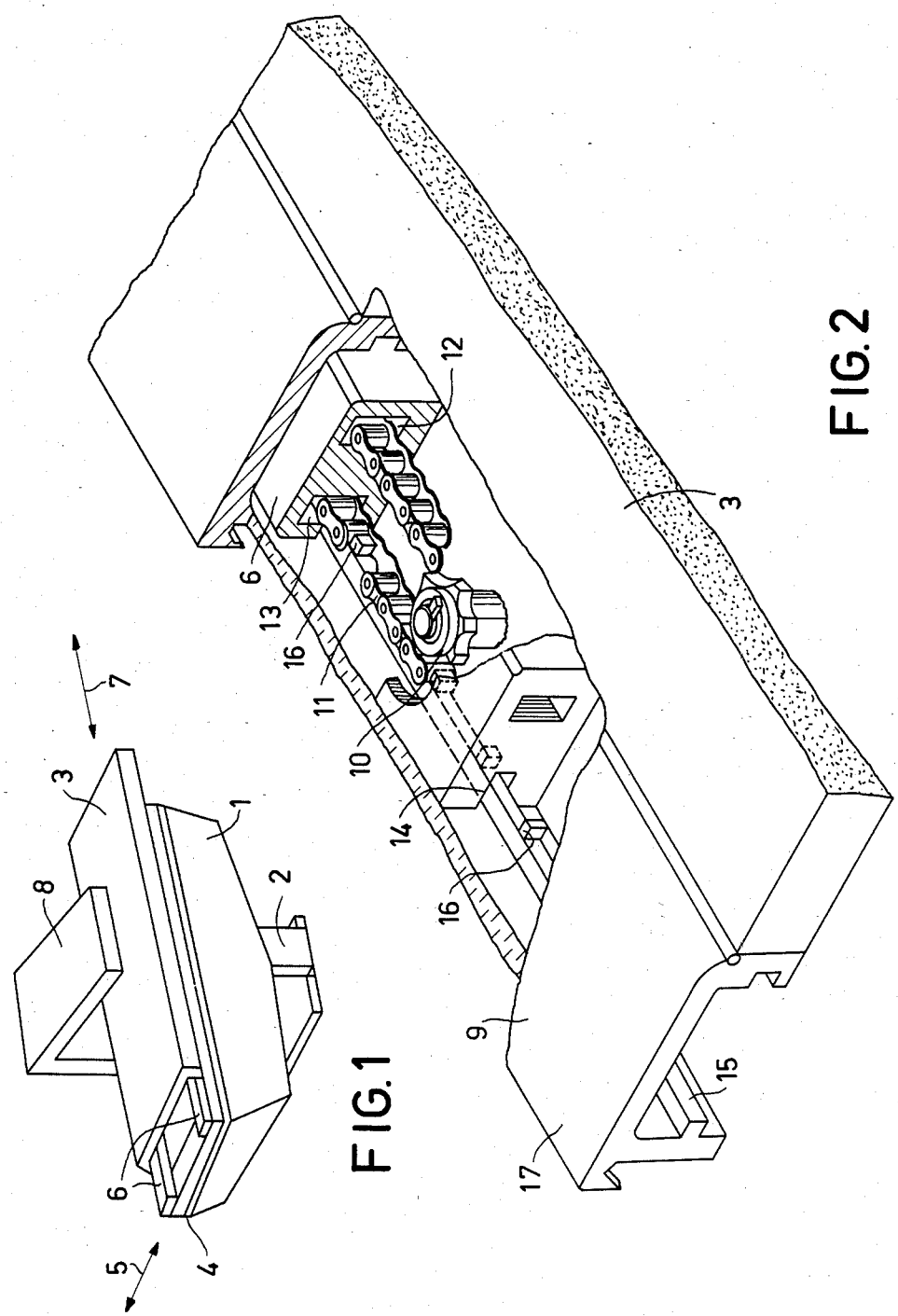

X-RAY APPARATUS COMPRISING A TABLE-TOP WHICH IS DISPLACEABLE IN THE LONGITUDINAL DIRECTION

BACKGROUND OF THE INVENTION

The invention relates to a patient table for an X-ray apparatus. The table has a tabletop which is displaceable in its longitudinal direction. The table top is coupled to an endless chain. The sprockets is guided by sprockets which are arranged so as to be spaced apart in the longitudinal direction. One of the sprockets driven by a motor.

An X-ray apparatus of this kind is known from U.S. Pat. No. 3,473,024 (Feiertag). In this apparatus, the chain and the table top are coupled by a coupling piece which is inserted in the chain and which is rigidly connected to the table top.

It is a drawback of the known X-ray apparatus that the stroke of the table top (i.e. the maximum possible displacement of the table top in the longitudinal direction) is smaller than the distance between the sprockets. Consequently, this stroke is limited to approximately 1.5 meters in practice.

SUMMARY OF THE INVENTION

It is an object of the invention to construct an X-ray having a larger stroke for the same distance between the sprockets.

This object is achieved, according to, the invention by providing the table top with coupling elements which engage the chain like a comb. The coupling elements are arranged so as to be offset with respect to one another in the longitudinal direction of the table top. The coupling elements may consist of, for example, suitable shaped pins which are attached to the table top. However, they are preferably formed by the teeth of a toothed rack.

Consequently, according to the invention the table top is no longer rigidly connected to the chain. The table top engages the chain by the coupling elements. The table top can in theory be displaced beyond the head end or foot end so far that the chain is still engaged by at least one coupling element only.

BRIEF DESCRIPTION OF THE DRAWING

FIG. 1 is a perspective view of an X-ray apparatus according to the invention.

FIG. 2 is a perspective view of a detail of the apparatus of FIG. 1.

DESCRIPTION OF THE PREFERRED EMBODIMENTS

FIG. 1 shows an X-ray apparatus whose frame is journalled so as to be tiltable about a horizontal axis in a base construction 2. The frame supports a laterally arranged carriage 4 which is displaceable parallel to the tilt axis, i.e. in the direction of the double arrow 5. Carriage 4 comprises two parallel guide rails 6 which extend perpendicularly to the axis 5. Guide rails 6 serve to guide a table top 3 in its longitudinal direction, i.e. in the direction of the double arrow 7.

The X-ray apparatus also comprises an imaging section.

The table 3 is displaced by means of a chain, which is not shown in FIG. 1. The chain is driven via a motor and a sprocket, which also are not shown in FIG. 1.

As appears from FIG. 2, in each of the guide rails 6 there are arranged two sprockets 10. Sprockets 10 are arranged near the opposite ends of the guide rails 6. The axis of rotation of each sprocket is perpendicular to the plane of the table top An endless chain loop 11 is guided around the sprockets 10 in each guide rail 6. The chain is guided in ducts 12 and 13 which extend longitudinally in each guide rail 6. The duct 13, i.e. the outer one of the two ducts, is provided on its outer side with a slit 14. Slit 14 extends across the full length of the guide rail 6.

The slit 14 is penetrated by a toothed rack 15. Rack 15 also extends in the longitudinal direction. At least some of the teeth 16 of rack 15 engage the chain 11 without being rigidly connected thereto.

The toothed rack 15 forms part of a rail 9 on the long side of the table top 3. The table top is displaced in the longitudinal direction by driving one of the sprockets 10 by means of a motor (not shown). The force exerted on the chain 11 by the sprocket is transferred to the teeth 16. As a result the table-top 3 is displaced in the longitudinal direction.

When the toothed rack 15 is comparatively long, or when the table top 3 is displaced far in the direction of the head end or the foot end, the teeth 16 of the toothed rack 15 could collide with the teeth of the sprocket 10. The risk of such a collision can be mitigated by arranging the sprockets 10 and the toothed rack 15 so as to be offset perpendicularly to the table top 3 so that their teeth extend in different planes which are parallel to the plane of the table top.

Alternatively, according to a preferred solution to this problem the distance between two adjacent teeth 16 of the toothed rack 15 amounts, to twice the pitch of the chain (i.e. twice the length of the chain divided by the number of links). The teeth of the sprockets 10 are then offset so that they engage only every other chain link. Then, the toothed rack 15 is arranged to engage only the chain links which cannot be engaged by the teeth of the sprockets 10. Collision between the teeth is then impossible.

The distances between the teeth 16 of the toothed rack 15 could in principle, also amount to four times the pitch of the chain. It is alternatively possible to provide the sprockets with so few teeth that only every third link can be engaged by a tooth. In that case the teeth of the toothed rack should also engage only every third (or sixth or ninth) chain link.

The described coupling between the table top 3 and the chain 11 produces forces which deflect the chain perpendicularly to its direction of movement. However, the guiding of the chain 11 in the ducts 12 and 13 prevents the chain from being deflected so far that is can no longer be engaged by the toothed rack.

The other guide rail is constructed as a mirror image of the rail shown in FIG. 2, and it is enclosed by a profiled rail on the other long side of the table top which is also a mirror image of rail 6. The chain in this other guide rail is driven at the same speed as the chain shown in FIG. 2, but in the opposite direction.

The guide rails perform three functions; (i) guiding the chains, (ii) serving as a guide for the rails and hence for the table top, and (iii) preventing the lifting of the table top in that the toothed racks 15 engage the slits 14.

According to the invention, the stroke of the table top can be increased by almost twice the distance between the two extreme coupling elements. However, in practice such a long stroke is not usually necessary.

What is claimed is:

1. A patient table for an X-ray apparatus, said table comprising:
   a carriage;
   a table top slidably arranged on the carriage to be displaceable in a longitudinal direction;
   at least two rotatable sprockets arranged on the carriage and spaced from each other in the longitudinal direction, each sprocket having teeth;
   a motor for rotating one of the sprockets;
   an endless chain loop arranged around the sprockets, said chain having links engaged by the teeth of the sprockets; and
   a plurality of coupling elements attached to the table top, said coupling elements being spaced from each other in the longitudinal direction and being arranged to engage the chain links;
   characterized in that:
   the chain has a pitch equal to the length of the chain divided by the number of links in the chain;
   adjacent teeth of the sprockets are separated circumferentially by a distance equal to twice the pitch of the chain so that the teeth of the sprockets engage only every other chain link;
   adjacent coupling elements are separated by a distance equal to twice the pitch of the chain so that the coupling elements engage only every other chain link; and
   the coupling elements engage only links which are not engaged by the teeth of the sprockets.

2. A patient table as claimed in claim 1, characterized in that the coupling elements are the teeth of a rack which is rigidly connected to the table top.

3. A patient table as claimed in claim 2, characterized in that the table further comprises a guide rail arranged on the carriage to limit deflection of the chain where the chain is engaged by the coupling elements.

4. A patient table as claimed in claim 3, characterized in that the guide rail has two ducts for guiding the chain, and the guide rail has a slit communicating with one duct, the coupling elements engaging the chain through the slit.

5. A patient table as claimed in claim 4, characterized in that the rack comprises a rail to which the teeth of the rack are affixed, the rail being slidably arranged on the slit in the guide rail.

* * * * *